(12) United States Patent
Zelisko et al.

(10) Patent No.: US 8,383,755 B2
(45) Date of Patent: Feb. 26, 2013

(54) ENZYME-MEDICATED CROSS-LINKING OF SILICONE POLYMERS

(75) Inventors: Paul M. Zelisko, Stoney Creek (CA); Karen Arnelien, Calgary (CA); Mark Frampton, Thorold (CA)

(73) Assignee: Brock University, St. Catherines (CA)

( * ) Notice: Subject to any disclaimer, the term of this patent is extended or adjusted under 35 U.S.C. 154(b) by 168 days.

(21) Appl. No.: 12/664,195

(22) PCT Filed: Jun. 19, 2008

(86) PCT No.: PCT/CA2008/001150
§ 371 (c)(1),
(2), (4) Date: Jun. 28, 2010

(87) PCT Pub. No.: WO2008/154731
PCT Pub. Date: Dec. 24, 2008

(65) Prior Publication Data
US 2010/0283183 A1 Nov. 11, 2010

Related U.S. Application Data

(60) Provisional application No. 60/944,893, filed on Jun. 19, 2007.

(51) Int. Cl.
*C08G 77/08* (2006.01)
(52) U.S. Cl. .......................................... 528/12; 528/21
(58) Field of Classification Search .................. 528/12, 528/21
See application file for complete search history.

(56) References Cited

U.S. PATENT DOCUMENTS

| | | | |
|---|---|---|---|
| 6,670,438 B1 | 12/2003 | Morse et al. | |
| 7,335,717 B2 | 2/2008 | Morse et al. | |
| 2005/0090634 A1 | 4/2005 | Morse et al. | |
| 2005/0196849 A1* | 9/2005 | Brandstadt et al. | 435/131 |
| 2007/0254141 A1 | 11/2007 | Morse et al. | |

FOREIGN PATENT DOCUMENTS

| | | |
|---|---|---|
| EP | 2246435 A1 | 11/2010 |
| WO | 0035993 A1 | 6/2000 |
| WO | 0187825 A1 | 11/2001 |
| WO | 2006071772 A2 | 7/2006 |
| WO | 2006137915 A2 | 12/2006 |
| WO | 2008154731 A1 | 12/2008 |

OTHER PUBLICATIONS

Zelisko et al., "Trypsin-catalyzed cross-linking of alpha,omega-triethoxysilyl-terminated polydimethylsiloxane: an experimental and computational approach", Abstracts of Papers, 232nd ACS National Meeting, San Francisco, California, USA, Sep. 10-14, 2006, American Chemical Society, Washington, DC, USA, Abstract No. POLY 339.

Zelisko et al., "Trypsin-catalyzed cross-linking of alpha,omega-triethoxysilyl-terminated polydimethylsiloxane: an experimental and computational approach", San Francisco ACS Book Chapter, Apr. 5, 2007.

Zelisko et al., "Enzyme mediated cross-linking of silicone polymers", Polymer Preprints, Jul. 23, 2007, pp. 984-985, vol. 48, No. 2.

Zelisko and Brook, "Stabilization of alpha-Chymotrypsin and lysozyme entrapped in water-in-silicone oil emulsions", Langmuir, 2002, pp. 8982-8987, vol. 18, No. 23, American Chemical Society.

Frampton et al., "Enzyme-mediated sol-gel processing of alkoxysilanes", Chem. Commun., 2008, pp. 5544-5546, Issue 43, The Royal Society of Chemistry.

Zelisko, PM, "Protein-Silicone Interactions" (Presentation), Sep. 21, 2007, State University of New York, Buffalo, NY, USA.

Bassindale, AR; Brandstadt, KF; Lane, TH; Taylor, PG. Enzyme-catalysed siloxane bond formation. J. Inorg. Biochem., 2003, pp. 401-406, vol. 96, Nos. 2-3.

Margolin, AL. Novel crystalline catalysts. Trends Biotechnol., 1996, pp. 223-230, vol. 14, No. 7.

V. Braunmuehl, V; Jonas, G; Stadler, R. Enzymic Grafting of Amylose from Poly(dimethylsiloxanes). Macromolecules, 1995, pp. 17-24, vol. 28, No. 1, American Chemical Society.

Li, N; Zong, M-H; Liu, C; Peng, H-S, Wu, H-C. (R)-Oxynitrilase-catalysed synthesis of chiral silicon-containing aliphatic (R)-ketone-cyanohydrins. Biotechnol. Lett., 2003, pp. 219-222, vol. 25, Kluwer Academic Publishers.

Bond, R; Mcauliffe, JC. Silicon Biotechnology: New Opportunities for Carbohydrate Science. Aust. J. Chem., 2003, pp. 7-11, vol. 56, CSIRO Publishing.

Morse, DE. Silicon biotechnology: harnessing biological silica production to construct new materials. Trends Biotech., 1999, pp. 230-232, vol. 17, No. 6.

Patwardhan, SV; Mukherjee, N; Steinitz-Kannan, M; Clarson, SJ. Bioinspired synthesis of new silica structures. Chem. Commun., 2003, pp. 1122-1123.

Naik, RR; Whitlock, PW; Rodriguez, F; Brott, LL; Glawe, DD; Clarson, SJ; Stone, MO. Controlled formation of biosilica structures in vitro, Chem. Commun., 2003, pp. 238-239.

Patwardhan, SV; Clarson, SJ. Silicification and biosilicification, Silicon Chem., May 2002, pp. 207-214, vol. 1, No. 3.

Coradin, T; Coupé, A; Livage, J. Interactions of bovine serum albumin and lysozyme with sodium silicate solutions, Colloids Surf. B: Bioint., 2003, pp. 189-196, vol. 29.

Roth, KM; Zhou, Y; Yang, W; Morse, DE. Bifunctional Small Molecules Are Biomimetic Catalysts for Silica Synthesis at Neutral pH, J. Am. Chem. Soc., 2005, pp. 325-330, vol. 127.

(Continued)

*Primary Examiner* — Kuo-Liang Peng
(74) *Attorney, Agent, or Firm* — Osler, Hoskin & Harcourt LLP

(57) ABSTRACT

Disclosure herein are methods of preparing cross-linked silicone polymers by contacting a silicone polymer and optionally a cross-linking agent with a hydrolytic enzyme under conditions for the cross-linking of the silicone polymer, wherein the silicone polymer has been modified to comprise functional groups that react with the hydrolytic enzyme.

23 Claims, 9 Drawing Sheets

OTHER PUBLICATIONS

Perry, CC; Keeling-Tucker, T. Crystalline silica prepared at room temperature from aqueous solution in the presence of intrasilica bioextracts, Chem. Commun., 1998, pp. 2587-2588.

Curnow, P; Bessette, PH; Kisailus, D; Murr, MM; Daugherty, PS; Morse, DE. Enzymatic Synthesis of Layered Titanium Phosphates at Low Temperature and Neutral pH by Cell-Surface Display of Silicatein-α, J. Am. Chem. Soc., 2005, pp. 15749-15755, vol. 127.

Patwardhan, SV; Clarson, SJ. Bioinspired mineralisation: macromolecule mediated synthesis of amorphous germania structures, Polymer, May 26, 2005, pp. 4474-4479, vol. 46, No. 12.

Laronde, FJ; Brook, MA. Stereoselective reduction of ketones by histidine-alkoxysilane complexes: The role of imidazole in nucleophilic substitution at silicon, Tet. Lett., Apr. 30, 1999, pp. 3507-3510, vol. 40, No. 18.

Frampton, MB; Simionescu, R; Dudding, T; Zelisko, PM. The Enzymatic Cleavage of Si-O Bonds: A Kinetic Analysis of the Biocatalyzed Hydrolysis of Phenyltrimethoxysilane, J. Mol. Cat. B: Enzymatic, Sep. 2010, pp. 105-112, vol. 66, Nos. 1-2.

Chuit, C; Corriu, RJP; Reye, C; Young, JC. Reactivity of penta- and hexacoordinate silicon compounds and their role as reaction intermediates, Chem. Rev., Jun. 1993, pp. 1371-1448, vol. 93, No. 4.

Kakiuchida, H; Takahashi, M; Tokuda, Y; Masai, H; Yoko, T. Effects of Organic Groups on Structure and Viscoelastic Properties of Organic-Inorganic Polysiloxane Hybrid System, J. Phys. Chem. B., 2007, pp. 982-988, vol. 111, No. 5.

Kuniyoshi, M; Takahashi, M; Tokuda, Y; Yoko, T. Hydrolysis and polycondensation of acid-catalyzed Phenyltriethoxysilane (PhTES), J. Sol-Gel Sci. Technol., 2006, pp. 175-183, vol. 39, No. 2.

Takahashi, K; Tadanaga, K; Matsuda, A; Hayashi, A; Tatsumisago, M. Effects of Phenyltriethoxysilane Concentration in Starting Solutions on Thermal Properties of Polyphenylsilsesquioxane Particles Prepared by a Two-Step Acid-Base Catalyzed Sol-Gel Process, J. Ceramic Soc. Japan, 2007, pp. 131-135, vol. 115.

Yang, Z; Liang, G; Xu, B. Enzymatic Hydrogelation of Small Molecules. Acc. Chem. Res., Feb. 2008, pp. 315-326, vol. 41, No. 2, American Chemical Society.

Wojtach, K; Laczka, M; Cholewa-Kowalska, K; Olejniczak, Z; Sokolowska, J. Characteristics of colored inorganic—organic hybrid materials, J. Non-Cryst. Solids, Jun. 15, 2007, pp. 2099-2103, vol. 353.

Buisson, P; EL Rassy, H; Maury, S; Pierre, AC. Biocatalytic Gelation of Silica in the Presence of a Lipase, J. Sol-Gel Sci. Technol., Jul. 2003, pp. 373-379, vol. 27, No. 3.

Favre, N; Ahmad, Y; Pierre, AC. Biomaterials obtained by gelation of silica precursor with $CO_2$ saturated water containing a carbonic anhydrase enzyme, J. Sol-Gel Sci. Technol., May 2011, pp. 442-451, vol. 58, No. 2.

Frampton, MB; Zelisko, PM. Organosilicon Biotechnology, Silicon, 2009, pp. 147-163, vol. 1, No. 3.

Frampton, M; Simionescu, R; Zelisko, PM. Enzyme-Mediated Synthesis of Silsesquioxanes, Silicon, 2009, pp. 47-56, vol. 1, No. 1.

Frampton, MB; Subczynska, I; Zelisko, PM. Biocatalytic Synthesis of Silicone Polyesters. Biomacromolecules, 2010, pp. 1818-1825, vol. 11, No. 7, American Chemical Society.

Frampton, MB; Zelisko, PM. A Comparison of Protease Active Sites and their Ability to Process Silicon-Based Substrates, Silicon, Apr. 21, 2011, Online First(TM), Springer.

Syldatk, C; Stoffregen, A; Brans, A; Fritsche, K; Andree, H; Wagner, F; Hengelsberg, H; Tafel, A; Wuttke, F; Zilch, H; Tacke, R. Biotransformation as a new method for preparing optically active organometallic compounds. Annals of the New York Academy of Sciences, 1988, pp. 330-338, 542.

Bauer, P; Elbaum, R; Weiss, IM. Calcium and silicon mineralization in land plants: Transport, structure and function, Plant Science, Jun. 2011, pp. 746-756, vol. 180, No. 6.

Hazelaar, S; Van Der Strate, HJ; Gieskes, WWC; Vrieling, EG. Possible role of ubiquitin in silica biomineralization in diatoms: identification of a homologue with high silica affinity. Biomolecular Engineering, 2003, pp. 163-169, vol. 20, Elsevier Science B.V.

Vrieling, EG; Beelen, TPM; Van Santen, RA; Gieskes, WWC. Diatom silicon biomineralization as an inspirational source of new approaches to silica production, Journal of Biotechnology, Apr. 1999, pp. 39-51, vol. 70.

Eliseeva, T; Panzner, MJ; Youngs, WJ; Tessier, CA. Synthesis and characterization of imidazole-triphenylsilane complexes, Journal of Organometallic Chemistry, May 15, 2010, pp. 1507-1512, vol. 695.

Schröder, HC; Wang, X; Tremel, W; Ushijima, H; Müller, WEG. Biofabrication of biosilica-glass by living organisms, Natural Product Reports, 2008, pp. 455-474, vol. 25.

Sumper, M; Brunner, E. Silica Biomineralisation in Diatoms: The Model Organism *Thalassiosira pseudonana*, Chem. Bio. Chem., 2008, pp. 1187-1194, vol. 9, No. 8.

Jiang, W; Chu, X; Wang, B; Pan, H; Xu, X; Tang, R. Biomimetically Triggered Inorganic Crystal Transformation by Biomolecules: A New Understanding of Biomineralization, Journal of Physical Chemistry B, 2009, pp. 10838-10844, vol. 113.

Abbate, Vincenzo; Bassindale, Alan R.; Brandstadt, Kurt F.; Lawson, Rachel, Taylor, Peter G.; Enzyme mediated silicon-oxygen bond formation; the use of *Rhizopus oryzae* lysozyme and phytase under mild conditions, Dalton Transactions, 2010, 39, 9361-9368.

Brunner Eike; Groger, Christian; Lutz, Katharina; Richthammer, Patrick; Apinde, Katrin; Sumper, Mandfred; Analytical studies of silica biomineralization: towards an understanding of silica processing by diatoms, Appl Microbiol Biotechnol (2009) 84: 607-616.

Zelisko, et al., "Trypsin-Catalyzed Cross-Linking of Triethoxysilyl-Terminated Polydimethylsiloxane: An Experimental and Computational Approach", Advances in Silicones and Silicone-Modified Materials, ACS Symposium Series; American Chemical Society, pp. 47-57, vol. 51, Nov. 9, 2010.

Patwardhan, "Biomimetic and bioinspired silica: recent developments and applications", Chem. Commun., 2011, 47, 7567-7582.

\* cited by examiner

Serine protease chemistry     Analogue to solution-phase silicon chemistry

Typical H-bond distance ~1.80-2.00 Å

ENZYME-MEDICATED CROSS-LINKING OF SILICONE POLYMERS

This application is a National Stage of International Application No. PCT/CA2008/001150 filed Jun. 19, 2008, which claims the benefit of Provisional Application No. 60/944,893, filed Jun. 19, 2007, the contents of both of which are herein incorporated in their entirety by reference.

FIELD OF THE DISCLOSURE

The present disclosure relates to methods of preparing cross-linked silicone polymers, in particular via enzyme catalysis.

BACKGROUND OF THE DISCLOSURE

Silicon is one of the most abundant elements in the Earth's crust. Nature has made use of silica in biological environments both as an essential nutrient and as the skeleton of certain marine organisms.[1,2] Controlled silica formation has been accomplished in vitro using mammalian digestive enzymes.[3] Although enzymes have been used to form carbohydrate-modified silicones, the cross-linking of silicone polymers using enzymes has not been examined.[4]

Tin catalysts are often employed in the cross-linking of silicones, however, given the interest in using silicones as biomaterials, the use of potentially toxic tin compounds as catalysts can be limiting in this regard.[5,6] Silicones and proteins are not incompatible species.[5(c),7] Research conducted by both Morse et al. and Bassindale et al. has demonstrated the ability of silicatein and trypsin, respectively, to catalyze the hydrolysis and subsequent condensation of tetramethoxy- and tetraethoxysilanes.[3,8] These experiments have focused almost exclusively on the ability of enzymes/proteins to generate inorganic silica species.

SUMMARY OF THE DISCLOSURE

The present disclosure describes the use of enzymes as catalysts for the cross-linking of silicones in place of the more toxic catalyst systems such as those based on tin. Trypsin and pepsin effectively catalyzed the cross-linking of α,ω-(triethoxysilyl)ethyl-polydimethylsiloxane (TES-PDMS), similar to dibutyltin dilaurate; $^{29}$Si—NMR experiments revealed little difference between the products of the dibutyltin dilaurate- and trypsin-catalyzed systems.

Accordingly, the present disclosure relates to a method of preparing cross-linked silicone polymers comprising contacting a silicone polymer with a hydrolytic enzyme under conditions for the cross-linking of the silicone polymer, wherein the silicone polymer has been modified to comprise functional groups that react with the hydrolytic enzyme. In another aspect of the disclosure the method of preparing cross-linked silicone polymers further comprises a cross-linking agent.

It has been shown that it is possible to use enzymes as a means of cross-linking silicone polymers. The ability to generate cross-linked silicone systems using enzymes rather than potentially toxic heavy metal catalysts has a great deal of potential in silicone chemistry, both from synthetic and environmental vantage points. Hydrolytic enzymes provide an alternative to, for example, dibutyltin dilaurate in the cross-linking of silicone polymers. Enzymes have the potential to act as "green" catalysts in the synthesis of silicone-based materials.

The cross-linked polymers prepared herein find use in many applications, for example, but not limited to, drug delivery, biomedical devices, agricultural products, wound care, wound management, encapsulation technology, environmentally-friendly silicone synthesis and paper coatings.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION OF THE DISCLOSURE

Various cross-linking methodologies may be utilized to convert silicone polymer chains into more complex, 3-dimensional structures. These network structures such as gels (or hydrogels), films, elastomers, and interpenetrating polymer networks (IPNs) are useful in many applications. It has been shown that hydrolytic enzymes, such as trypsin and pepsin, effectively catalyze the cross-linking of α,ω-(triethoxysilyl) ethyl-polydimethylsiloxane (TES-PDMS), like dibutyltin dilaurate. $^{29}$Si-nuclear magnetic resonance (NMR) experiments revealed little difference between the products of the dibutyltin dilaurate-catalyzed and tryspin-catalyzed silicone systems. These data indicate that through the judicious use of ubiquitous enzymes, it is possible to generate cross-linked silicones that can be used in contact with biological systems; any decomposition products from the silicones would be as benign as sand and egg white, thereby providing a very "green" alternative to the metal catalyst systems.

Accordingly, the present disclosure includes a method of preparing cross-linked silicone polymers comprising contacting a silicone polymer with a hydrolytic enzyme under conditions for the cross-linking of the silicone polymer, wherein the silicone polymer has been modified to comprise functional groups that react with the hydrolytic enzyme. In a further aspect of the disclosure the method of preparing cross-linked silicone polymers further comprises a cross-linking agent.

The term "hydrolytic enzyme" refers to any enzyme that catalyzes the hydrolysis of a chemical bond with the participation of a water molecule. In embodiments of the present disclosure, the hydrolytic enzyme is a protease. A protease is any enzyme that catalyzes hydrolysis of a peptide bond. In a further embodiment, the protease is a cysteine protease. In a suitable embodiment the protease is selected from pepsin, trypsin, α-chymotrypsin, bromelain and papain, suitably pepsin or trypsin.

Figure 1:
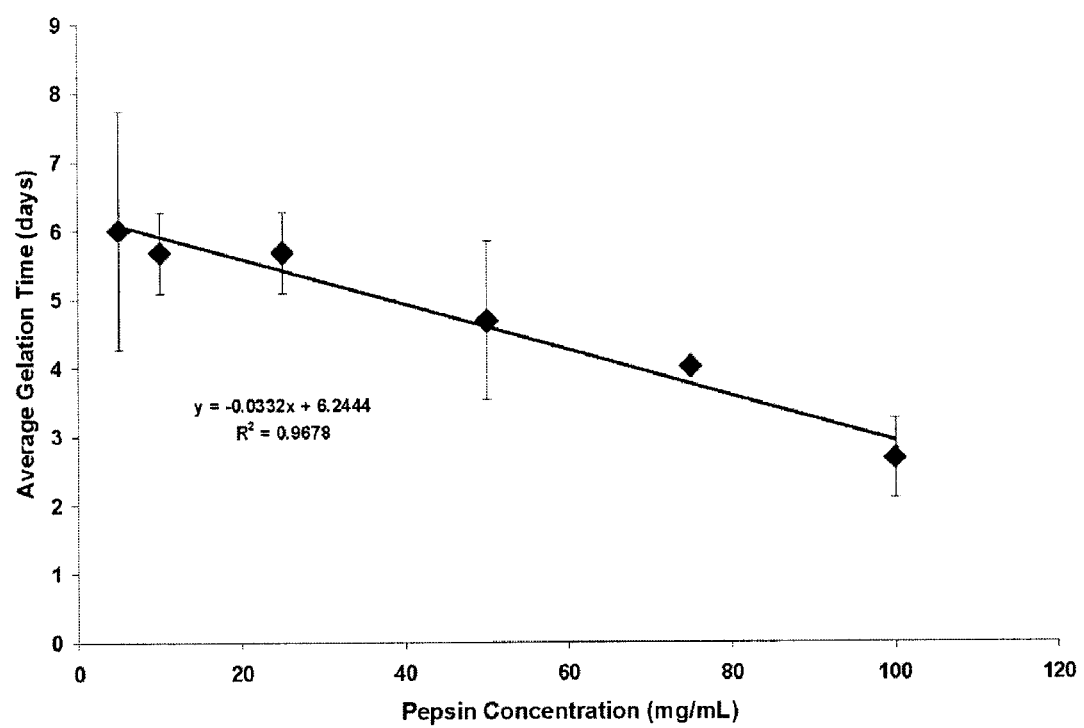
FIG. 1 is a graph showing the rate of cross-linking (gelation) of TES-PDMS relative to the concentration of pepsin.

In a further embodiment of the disclosure the enzyme is a native enzyme. FIG. 1 demonstrates the activity of the native enzymes serine protease and carboxy peptidase as compared to the isolated amino acids histidine and serine and to the control sample having no catalyst at all. Cross-linked polymer (visible as a white precipitate) formed in the vials containing serine protease and carboxy peptidase but not in the vials containing histidine or serine.

In a further aspect of the disclosure the enzyme may be derived from fruits. In a particular embodiment the cysteine protease enzyme, bromelain, can be derived from pineapple. The fruit enzymes may be purified before use or extracts of the leaves skin or fruit containing the enzyme may be used directly to effect cross-linking of the silicone polymers.

The term "contacting" as used herein means that the reagents are brought together by any means that result in the cross-linking of the silicone polymer. In an embodiment of the disclosure, the reagents are contacted by mixing, for example, by agitating or stirring, in a reaction vessel.

In an embodiment of the present disclosure, the cross-linking agent is of the formula $SiX_4$, wherein X is any hydrolysable group and each X may be the same or different. Suitably, each X is the same and is OR, wherein R is $C_{1-6}$alkyl. The term "alkyl" as used herein means straight and/or branched chain, saturated alkyl groups containing from one to 6 carbon atoms and includes methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like. Suitably R is methyl or ethyl.

It is another embodiment of the present disclosure that the functional groups on the silicone polymer are of the formula $L-SiX'_3$, wherein L is a linker group and X' is any hydrolysable group and each X' may be the same or different. Suitably, each X' is the same and is OR', wherein R' is $C_{1-6}$alkyl and alkyl is as defined above for R. Suitably R' is methyl or ethyl. A person skilled in the art would appreciate that L could be any suitable linking group that does not interfere with the cross-linking reaction catalyzed by the enzyme. In an embodiment of the disclosure L is $C_{1-10}$alkylene, wherein alkylene refers to a divalent straight and/or branched chain, saturated alkyl group containing from one to 10 carbon atoms and includes methylene, ethylene, propylene, n-hexylene and the like. Suitably, L is ethylene or methylene. In a further embodiment of the present disclosure, the function groups on the silicone polymer comprise carboxylic acids.

A person skilled in the art would appreciate that the method of the present disclosure can be applied to any suitable silicone polymer. In an embodiment of the disclosure the silicon polymer is polydimethylsiloxane.

In an embodiment of the disclosure the method of preparing cross-linked silicone polymers comprises contacting a silicone polymer with a hydrolytic enzyme under conditions for cross-linking of the silicone polymer optionally in a solvent.

In another embodiment of the disclosure, the method of preparing cross-linked silicone polymers comprises:
(a) mixing the silicone polymer and a cross-linking agent, optionally in a solvent, to provide a first mixture; and
(b) contacting the first mixture with the hydrolytic enzyme, optionally in water, buffer, or organic solvent, under conditions for the cross-linking of the silicone polymer.

In an embodiment of the disclosure, the conditions for the cross-linking of the silicone polymer comprise a temperature in the range of about 20° C. to about 40° C., suitably about 37° C.

Figure 2:
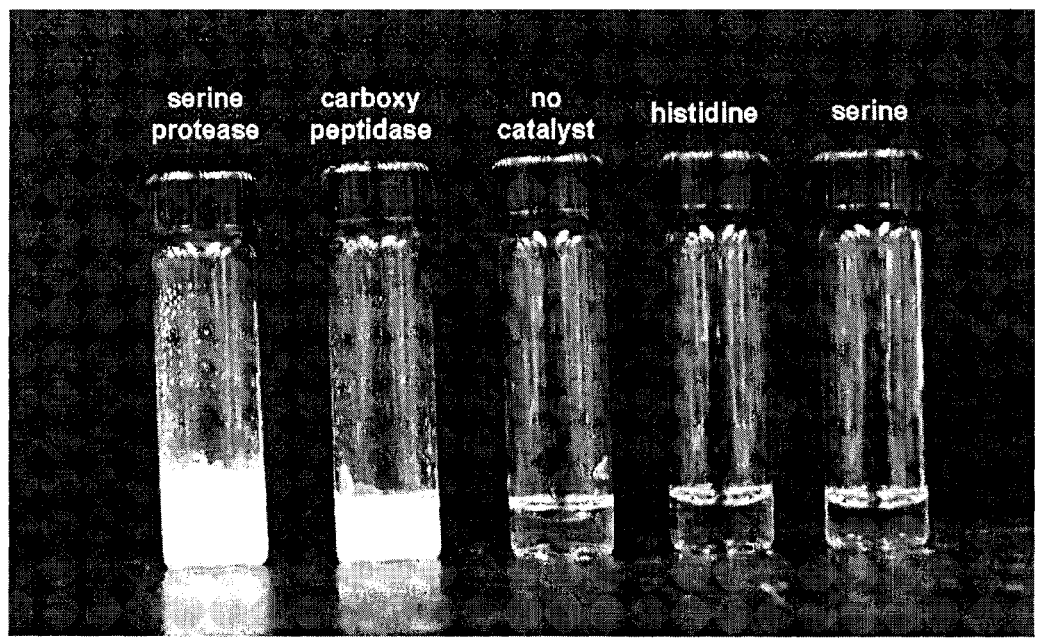
FIG. 2 shows the reaction of TES-PDMS in the presence of serine protease, carboxy peptidase, no catalyst, histidine and serine.

In a further aspect of the disclosure it has been found that the concentration of the enzyme in the reaction mixture can affect the speed of cross-linking of the polymer. FIG. 2 shows that as the concentration of the enzyme pepsin increased, the time in days for the formation of elastomers based upon TES-PDMS decreased. The rate of formation of elastomers or cross-linking of the polymer, also known as "gelation", is dependent on concentration. It is a further embodiment of the invention that the concentration of the enzyme may be increased to increase the rate of cross-linking.

In a further embodiment of the disclosure the first mixture is contacted with the hydrolytic enzyme suitably by mixing for about 1 minute to about 10 minutes to form a second mixture. It is another embodiment of the present disclosure that, following formation of the second mixture, said second mixture is poured into a mold or is coated onto a substrate. The mold is suitably in the shape of the article that one wishes to make using the cross-linked silicone polymer and, likewise, the substrate is any article made of any suitable material upon which one wishes to form a layer of cross-linked silicone polymer.

Accordingly the present disclosure is also related to cross-linked silicon polymers prepared using the methods disclosed herein as well as substrates coated with such polymers.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The following non-limiting examples are illustrative of the present disclosure:

EXAMPLES

Reagents

Tetraethoxysilane (TEOS), vinyltriethoxysilane, hydride terminated polydimethylsiloxane (H-PDMS-H) (n=~7-8, 2-3 cSt, $M_n$=~580 g/mol and n=~270, 1000 cSt, $M_n$=~24000 g/mol), platinum divinyl-tetramethyldisiloxane complex (3-5% platinum concentration, Karstedt's catalyst) in vinyl-terminated polydimethylsiloxane (PDMS), and dibutyltin dilaurate were purchased from Aldrich. Bovine pancreatic trypsin (EC 3.4.21.4) was supplied by Sigma. Dichloromethane (DCM, $CH_2Cl_2$) was obtained from Calcdon. Distilled water ($dH_2O$) was used in all aqueous preparations. Scanning electron micrograph (SEM) images were acquired using an AMRAY 1600T scanning electron microscope and nuclear magnetic resonance (NMR) spectra were acquired using a Bruker AV600.

Example 1

Synthesis of α,ω-(triethoxysilyl)-ethyl-polydimethylsiloxane (TES-PDMS)

A low molecular weight TES-PDMS ($TES-PDMS_{580}$) and a high molecular weight TES-PDMS ($TES-PDMS_{24000}$) were used independently in the cross-linking experiments. The synthesis of TES-PDMS is described in detail elsewhere.[9]

Example 2

Preparation of the Trypsin Catalyst System

Trypsin was added to the reaction system either as a solution in $dH_2O$ or as a suspension in $CH_2Cl_2$. In both instances the trypsin was added to the appropriate solvent and placed in a sonicator for 1-2 min or simply mixed Example 3

Formulation of Cross-Linked Silicone Polymers

The general formulation of the cross-linked silicone involved combining commercially available TEOS (($CH_3CH_2O)_4Si$) with either $TES-PDMS_{580}$ or $TES-PDMS_{24000}$ in a sample vial and mixing vigorously by inversion. Immediately upon the cessation of mixing, the tin catalyst dibutyltin dilaurate or a trypsin catalyst was added to the sample vial containing the silicon-based compounds. The vial was subsequently capped and the contents mixed for a further 5 min by inverting the vial end-over-end. Once the mixing cycle was complete, the contents were poured into either a small (3.5 cm diameter) Petri dish or a separate sample vial and were left uncovered for 30 min. The dish or vial cap was then replaced and the reaction was left covered on the lab bench at either ambient temperature or in an incubator at 37° Celsius. The exact amounts for the reagents used in the cross-linking experiments are outlined in Table 1. The formation of a macroscopically homogeneous solid inside the Petri dish or the sample vial was taken as evidence for cross-linking. Formulations containing both water and dichloromethane were also examined (Table 1). The cross-linking experiments were performed at both 21° C. and 37° C.

When the TEOS and TES-PDMS were combined in the absence of either dibutyltin dilaurate or trypsin (Table 1), no cross-liking was observed after a period of 2.5 months—only liquid was present; there was no evidence of elastomer or glass formation. Conversely, the addition of dibutyltin dilaurate to a solution of TEOS and TES-PDMS (Table 1, Entry 2) yielded a translucent solid in approximately 2-3 h. Even when water was added to $CH_2Cl_2$ and the mixture introduced into the formulations (Table 1, Entry 6), cross-linking of the silicone system was observed through the production of a translucent solid. Substituting trypsin for dibutyltin dilaurate in the cross-linking experiments (Table 1) resulted in cross-linking of the TEOS/TES-PDMS system being observed in approximately 48 h at 21° C. and approximately 18-20 h at 37° C. The increased rate of reaction at the elevated temperature was not unexpected given that the enzyme operates at 37° C. in vivo.[10] Given that the TEOS/TES-PDMS system cure time is on the order of months in the absence of any added rate-enhancing compounds, it can be concluded that this "background" rate is not responsible for the accelerated cure rate observed with the systems containing trypsin. Trypsin therefore expedited the hydrolysis and subsequent condensation of the alkoxysilyl moieties.

Experiments have also been performed to demonstrate that trypsin and pepsin effectively cross-link TES-PDMS in the absence of TEOS and that enzymes (e.g. bromelain) derived from fruits such as pineapple can also effect the same chemistry. Unpurified extracts from pineapple leaves, skin and fruit were also shown to cross-link TES-PDMS both in the presence and absence of TEOS.

Example 4

Imaging of Cross-Linked Silicone Systems

Figure 3:
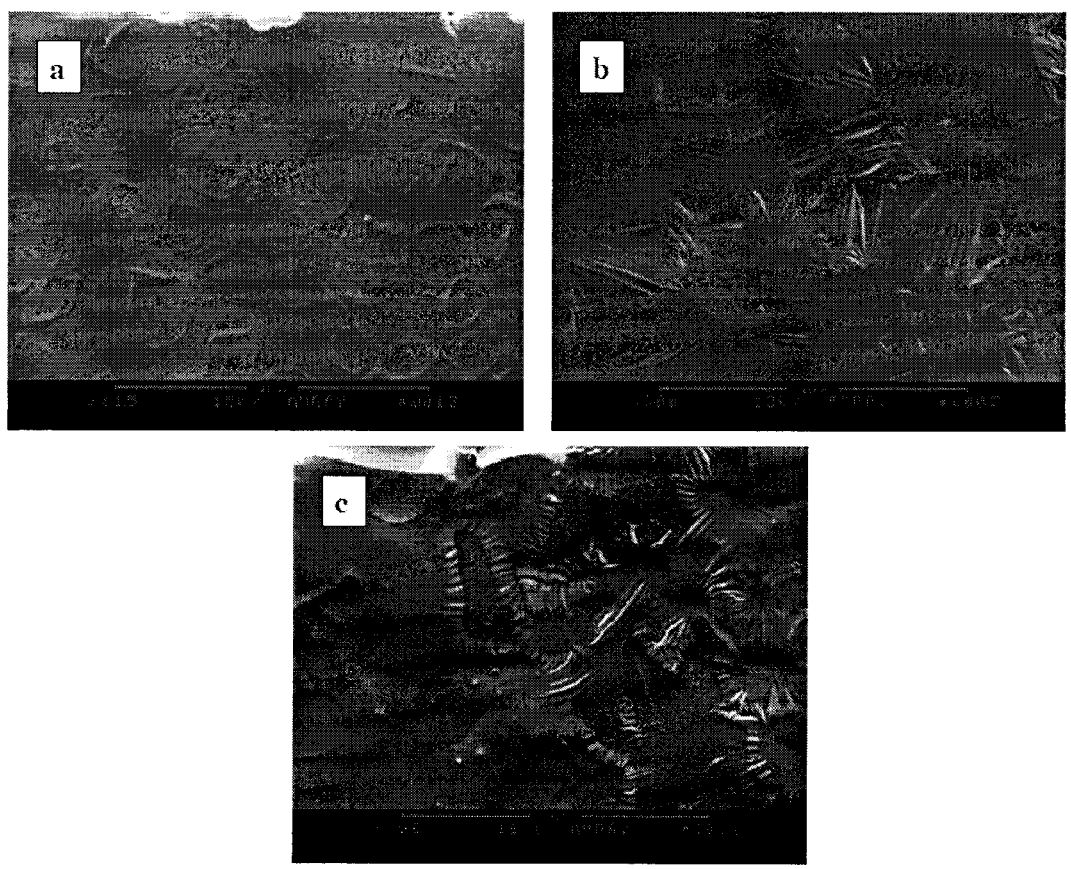
FIG. 3 shows SEM images of a cross-linked silicone system consisting of (a) TES-PDMS$_{580}$, TEOS, and dibutyltin dilaurate, (b) TEOS, TES-PDMS$_{24000}$, and trypsin, and (c) TEOS, TES-PDMS580 and trypsin.

In order to prepare the samples for SEM imaging, the sample was adhered to the SEM stub using a carbon adhesive. Once the sample was adhered to the stub, a conductive layer of gold and palladium was applied to the sample using a POLARON SC500 sputter coater. The samples were subsequently imaged using an AMRAY 1600T scanning electron microscope. Though the dibutyltin dilaurate- and trypsin-catalyzed systems appeared to be macroscopically homogeneous, SEM imaging of the samples revealed gross surface morphologies that differed from one sample to the other when the tin- and enzyme-catalyzed systems were compared (FIG. 3).

Example 5

$^{29}Si$ Solid-State NMR Analysis of the Cross-Linked Elastomers

NMR spectra of the silicone elastomers were acquired using a Bruker AV 600 spectrometer with a 4 mm magic angle spinning (MAS) broadband probe. The silicone elastomers were cooled using liquid nitrogen and crushed using a mortar and pestle prior to being added to a zirconium oxide rotor. The sample was spinning at 7000 Hz within the NMR probe. A delay (D1) of 10.0 s and a pulse with a 30° flip angle were employed. A total of 40,960 scans were collected for each sample at 298 K.

Figure 4:
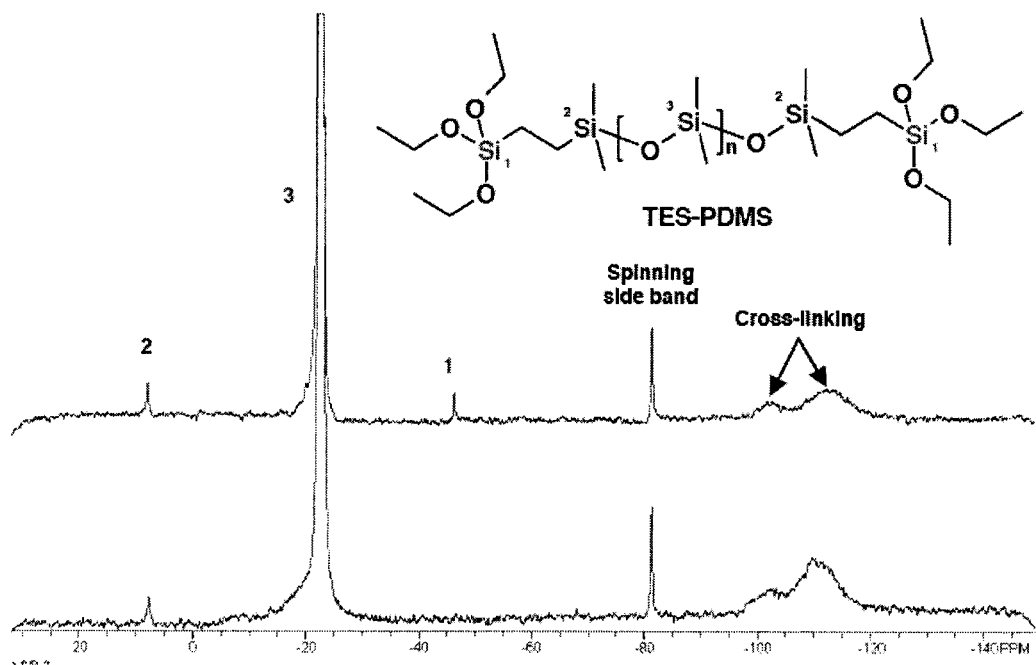
FIG. 4 shows the solid-state $^{29}$Si—NMR spectra of a trypsin cross-linked silicone elastomer (21° C.) (top) and a dibutyltin dilaurate cross-linked silicone elastomer (bottom).

A comparison of the $^{29}Si$ solid-state NMR spectra of the dibutyltin dilaurate- and trypsin-catalyzed silicone elastomers demonstrated striking similarities between the two systems (FIG. 4). In both instances a marked decrease in the resonance corresponding to the triethoxysilyl silicon atom and the evolution of signals indicative of cross-linking were observed. Based on the NMR experiments the trypsin-catalyzed system did not appear to be as efficient as the dibutyltin dilaurate-catalyzed system at room temperature based on the relative abundance of the triethoxysilyl silicon resonance (FIG. 4). The presence of a spinning side-band in the NMR spectra was confirmed by altering the frequency at which the sample was spinning.

Figure 5:
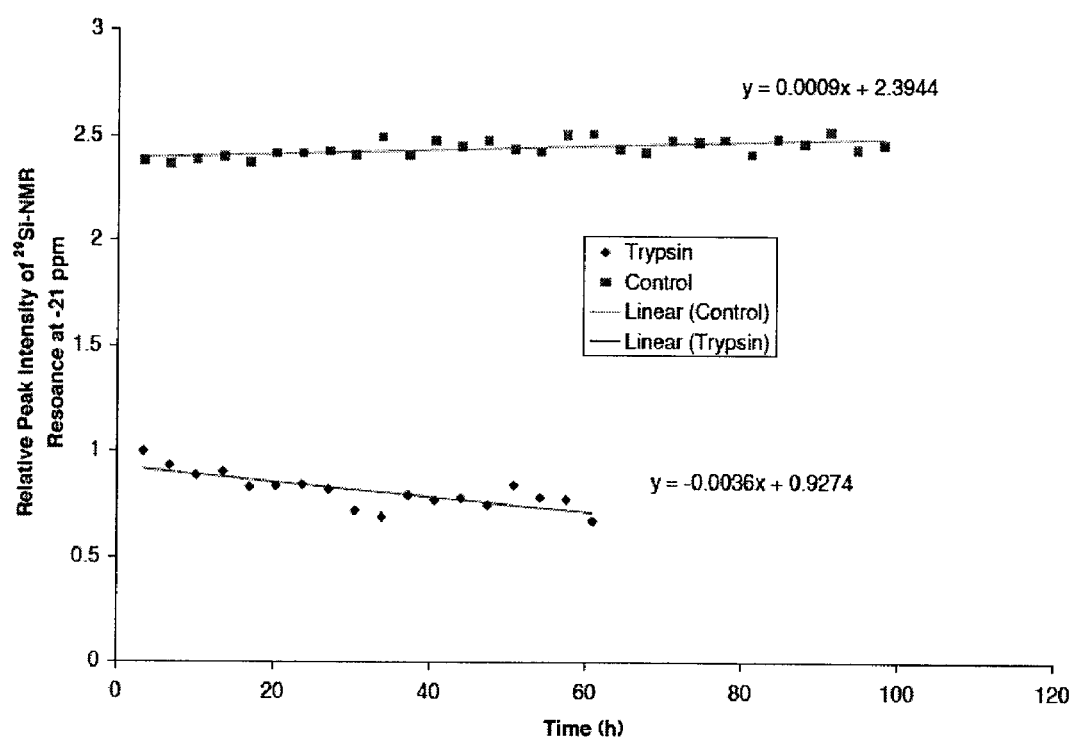
FIG. 5 is a graph showing the rate of cross-linking of triethoxysilyl-PDMS and TEOS in the presence and absence of trypsin.

Solution phase $^{29}Si$—NMR demonstrated that elastomer formation/cure was 10 times faster in the presence of trypsin than in the absence of any catalyst (FIG. 5)

Example 6

Computational Modeling

Computational studies using density functional theory (DFT) employing the gradient-corrected (B3LYP) hybrid functional of Becke-Lee-Yang and Parr[11] with a double zeta-potential 6-31G(d)[12] basis set as implemented by Gaussian 03 have been utilized to examine the chemistry within the enzymes' active site.

Figure 6:
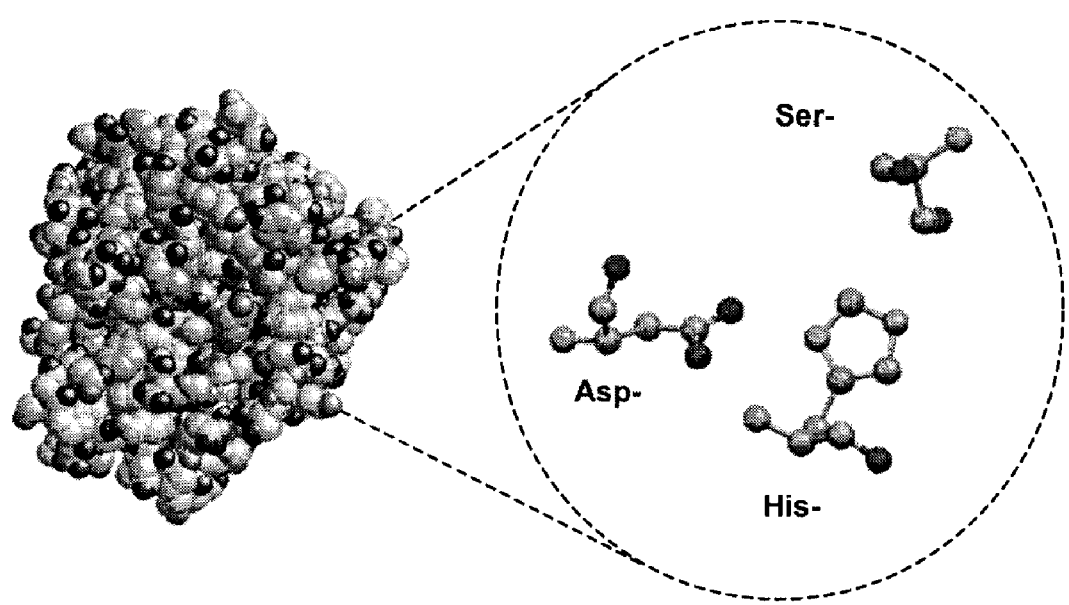
FIG. 6 shows the structure of bovine pancreatic trypsin and its catalytic triad (serine, histidine, and aspartic acid).
Figure 7:
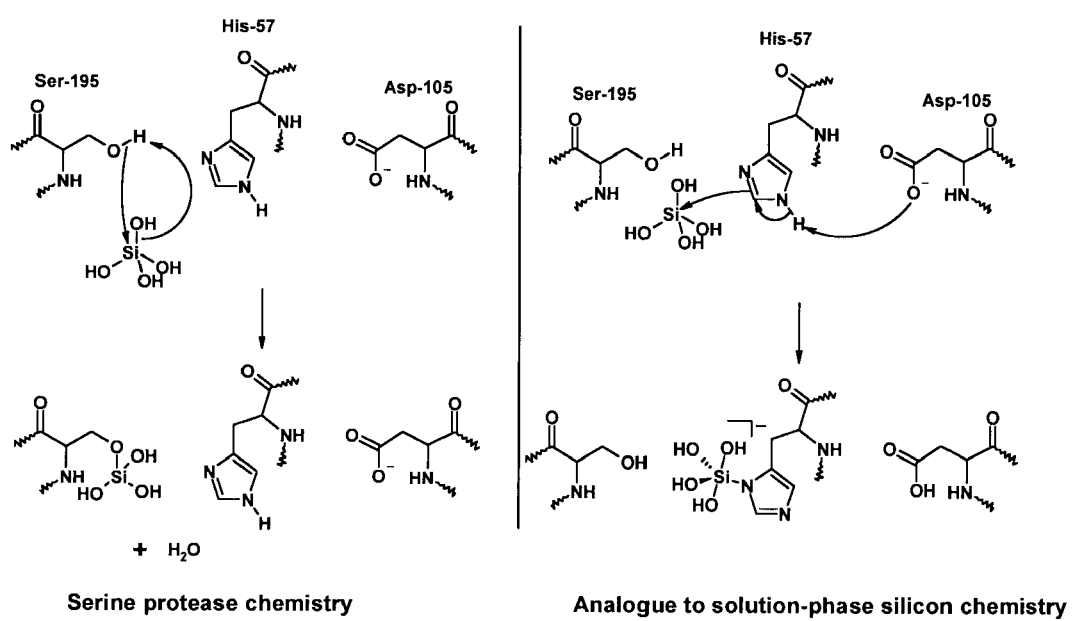
FIG. 7 shows two potential reaction pathways for the trypsin-catalyzed cross-linking of TEOS and TES-PDMS.

While not wishing to be limited by theory, upon examination of the trypsin catalytic triad (FIG. 6) it became apparent that two possible mechanisms could be used to account for the cross-linking of the TEOS/TES-PDMS by this serine protease:
1. Initial formation of a serine-silicon bond—an analogue of traditional trypsin chemistry (FIG. 7)
2. Initial formation of a histidine-silicon bond—an analogue of solution-phase silicon chemistry (FIG. 7).[13]

As a first principles approach toward addressing these fundamental mechanistic questions, preliminary theoretical studies have taken advantage of Houk's implementation of theozymes as truncated active site constructs for modeling enzyme catalysis. To facilitate this work electronic structure calculations using density functional theory employing the gradient-corrected (B3LYP) hybrid function of Becke-Lee-Yang and Parr with a double zeta-potential 6-31G(d) basis set as implemented in Gaussian 03 have been utilized.[14] For the purposes of these studies silicic acid $(Si(OH)_4)$ was used as a model compound as Bassindale et al.[3] have demonstrated that the hydrolysis of the alkoxysilyl moieties to silanols occurs on the surface of the enzyme, while the condensation of the silanols occurs within the active site.

Figure 8:
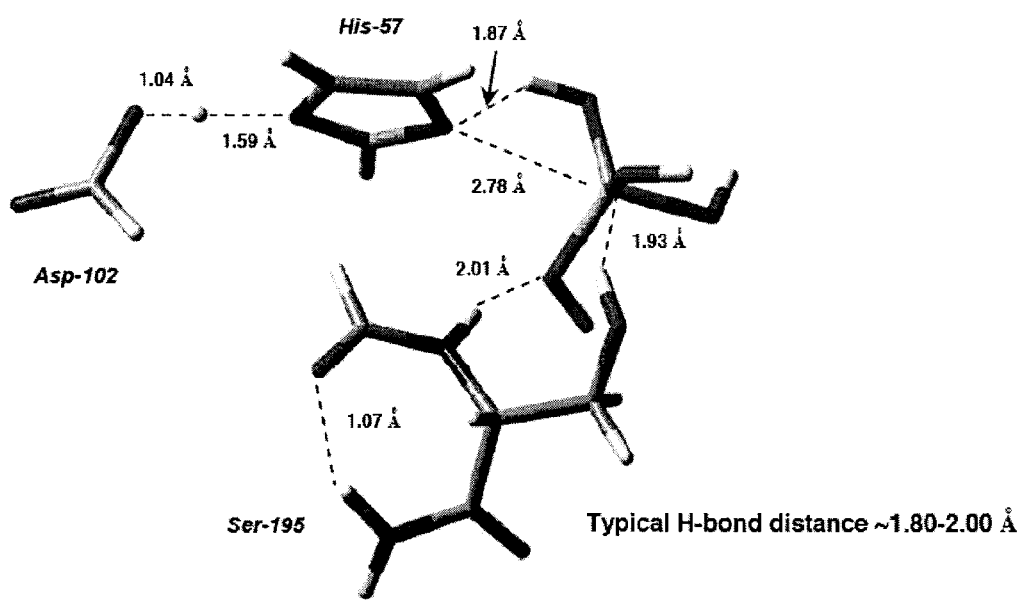
FIG. 8 shows a computational model of histidine addition to silicic acid in a trypsin theozyme.

The transition states for histidine addition (analogous to solution-phase silicon chemistry) (FIG. 8) and serine addition (serine protease mechanism) (FIG. 9) to the silicon atom have both been modeled.[15,17] Preliminary computational results suggest that serine and histidine addition are mechanistically rate determining. Analysis of the transition state energies for both possible mechanisms within a trypsin theozyme revealed that the addition of the serine residue is 3.72 kcal/mol (15.56 kJ/mol) more stable than the addition of the histidine residue, suggesting that serine addition to silicon is the preferred reaction mode for this condensation.

Figure 9:
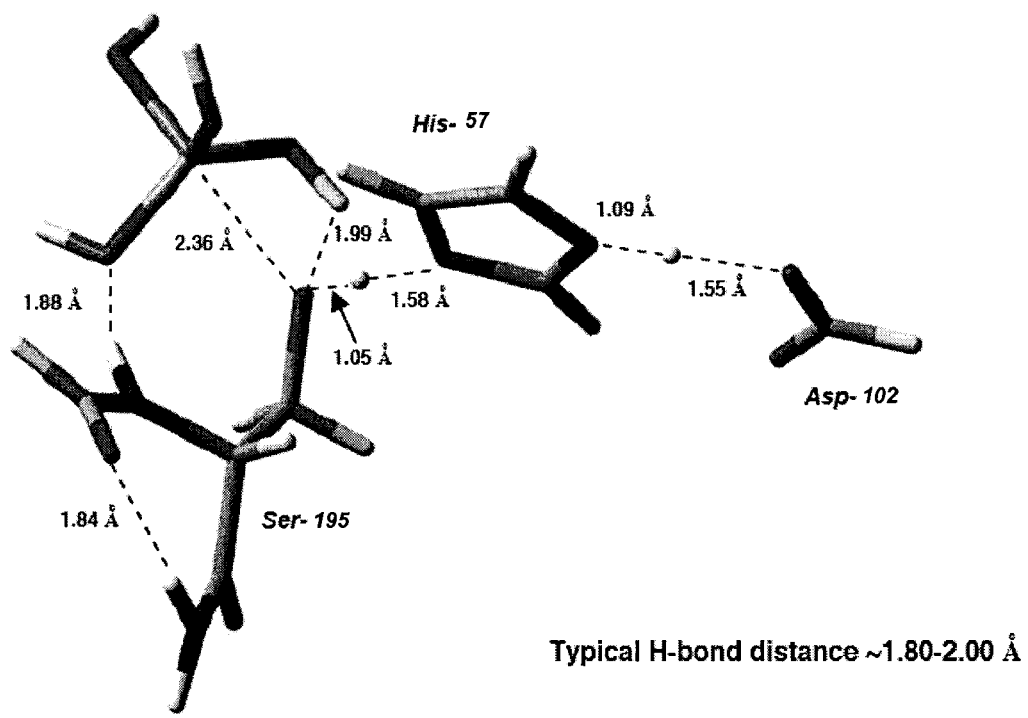
FIG. 9 shows a computational model of serine addition to silicic acid in a trypsin theozyme.

The latter observation is consistent with known Si—O (536 kJ/mol, 128 kcal/mol) versus Si—N (401 kJ/mol, 96 kcal/mol) bond strengths (FIG. 9).[15] Taken together the highlighted bond strengths and relative transition state energies suggest that the serine addition pathway is the operative mechanistic mode of catalysis. Perhaps the most interesting feature of the serine addition model is the Brønsted activation of the approaching silicic acid unit toward nucleophilic hydroxyl addition as a result of favorable (N—H . . . O) hydrogen bonding with the serine carboxy amide fragment (FIG. 9). As such it would appear that amide-hydroxyl hydrogen bond activation plays a critical role in facilitating silanol condensation.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Formulations used in silicone cross-linking experiments.

| Entry | Trypsin (g) | TEOS (g) | TES-PDMS-1$^a$ (g) | TES-PDMS-2$^b$ (g) | Sn$^c$ (g) | $H_2O$ (mL) | DCM (mL) | Temp (° C.) |
|---|---|---|---|---|---|---|---|---|
| 1 | — | 0.28 | 0.44 | — | — | — | — | 21 |
| 2 | — | 0.26 | 0.40 | — | 0.06 | — | — | 21 |
| 3 | 0.26 | 0.34 | 0.41 | — | — | 1.5 | — | 21 |
| 4 | 0.26 | 0.25 | — | 0.40 | — | — | 1.0 | 21 |
| 5 | 0.26 | 0.26 | — | 0.42 | — | 1.0 | 1.0 | 21 |
| 6 | — | 0.28 | 0.50 | — | 0.08 | 1.0 | 1.0 | 21 |
| 7 | — | 0.27 | 0.41 | — | — | 1.0 | — | 21 |
| 8 | — | 0.26 | 0.41 | — | — | 1.0 | 1.0 | 21 |
| 9 | 0.05 | 0.08 | 0.18 | — | — | 1.0 | — | 37 |
| 10 | 0.05 | — | — | — | — | 1.0 | — | 37 |
| 11 | 0.05 | 0.08 | 0.17 | — | — | 1.0 | 3.0 | 37 |

$^a$TES-PDMS$_{580}$;
$^b$TES-PDMS$_{24000}$;
$^c$dibutyltin dilaurate

FULL CITATIONS FOR DOCUMENTS REFERRED TO IN THE SPECIFICATION

1. Brook, M. A. *Silicon in Organic, Organometallic, and Polymer Chemistry,* 2000, John Wiley & Sons, Inc.: New York, N.Y.
2. (a) Kong, L.; Beattie, J. K.; Hunter, R. J. *Colloid Surf. B.,* 2003, 27, 11-21. (b) Peters, G. H. *Colloid Surf. B.,* 2002, 26, 84-101. (c) Simpson, T. L.; Volcani, B. E., Eds. *Silicon and Siliceous Structures in Biological Systems,* 1981, Springer Verlag New York, N.Y. (d) Kröger, N.; Lorenz, S.; Brunner, E.; Sumper, M. *Science,* 2002, 298, 584-586. (e) Kinrade, S. D.; Gilson, A. M. E.; Knight, C. T. G. *J. Chem. Soc. Dalton Trans.,* 2002, 307-309.
3. Bassindale, A. R.; Brandstadt, K. F.; Lane, T. H.; Taylor, P. G. *J. Inorg. Biochem.,* 2003, 96, 401-406.
4. Sahoo, B.; Brandstadt, K. F.; Lane, T. H.; Gross, R. A. *ACS Symposium Series,* 2005, 900 (Polymer Biocatalysis and Biomaterials), 182-190.
5. (a) Deyrail, Y.; Zydowicz, N.; Cassagnau, P. *Polymer,* 2004, 45, 6123-6131. (b) Park, J. H.; Bae, Y. H. *Biomaterials,* 2002, 23, 1797-1808. (c) Brook, M. A.; Zelisko, P. M.; Walsh, M. J.; Crowley, J. *Silicon Chem.,* 2002, 1, 99-106. (d) Wang, Q.; Gao, W.; Xie, Z. *J. Appl. Polym. Sci.,* 2003, 89, 2397-2399. (e) Tang, Y.; Tsiang, R. *Polymer,* 1999, 40, 6135-6146.
6. (a) Thayer, J. S. *Toxicity of Tin in Humans, in Handbook of Metal-Ligand in Biological Fluids: Bioinorganic Medicine,* Berthon, G. Ed. 1995, 2, 726-789.
7. (a) Liu, M.; Pacard, E.; Ragheb, A. M.; Zelisko, P. M.; Brook, M. A. *Stabilisation of Protein-Containing Water-in-Oil Emulsions* in *Cahiers de Formulation,* Lanteri, P.; Bordes, C., Eds. 2004, 11, 1542-162. (b) Zelisko, P. M.; Coo-Ranger, J. J.; Brook, M. A. *Polymer Preprints,* 2004, 45(1), 604-605. (c) Coo-Ranger, J. J.; Zelisko, P. M.; Brook, M. A. *Polymer Preprints,* 2004, 45(1), 674-675. (d) Liu, M.; Ragheb, A.; Zelisko, P.; Brook, M. A. *Preparation and Applications of Silicone Emulsions Using Biopolymers* in *Biomedical Applications of Polymer Colloids.* 2003. Chapter 11, pages 309-329. Elaïssari, A., Ed. (e)

Brook, M. A.; Bartzoka, V.; Zelisko, P.; Walsh, M. *Silicone-Protein Copolymers: Controlling Interfacial and Protein Stabilization in Organosilicone Chemistry: From Molecules to Materials*, 2003, Vol. 5, 606-611. Auner, N; Weis, J, Eds. (f) Zelisko, P. M.; Bartzoka, V.; Brook, M. A. *Exploiting Silicone-Protein Interactions: Stabilization Against Denaturation at Interfaces in Symposium Series No.* 838 *Synthesis and Properties of Silicones and Silicone-Modified Materials*, Clarson, S. J.; Fitzgerald, J. J.; Owen, M. J.; Smith, S. D.; Van Dyke, M. E. Eds. 2003. Chapter 19, 212-221. (g) Zelisko, P. M.; Brook, M. A. *Langmuir,* 2002, 18(23), 8982-8987.

8. (a) Zhou, Y.; Shimizu, K.; Cha, J. N.; Stucky, G. D.; Morse, D. E. *Angew. Chem. Int. Ed.,* 1999, 38, 779-782. (b) Cha, J. N.; Shimizu, K.; Zhou, Y.; Christiansen, S. C.; Chmelka, B. F.; Stucky, G. D.; Morse, D. E. *Proc. Natl. Acad. Sci. USA,* 1999, 96, 361-365.

9. Bartzoka, V.; Chan, G.; Brook, M. A. *Langmuir,* 2000, 16, 4589-4593.

10. (a) Brown, W.; Wold, F. *Biochem.,* 1973, 12, 828-834. (b) Brown, W.; Wold, F. *Biochem.,* 1973, 12, 835-840.

11. (a) Becke, A. D. *J. Chem. Phys.,* 1993, 98, 1372-1377. (b) Becke, A. D. *J. Chem. Phys.,* 1993, 98, 5648-5652. (c) Lee, C.; Yang, W.; Parr, R. G. *Phys. Rev. B.,* 1998, 37, 785-789.

12. (a) Ditchfield, R.; Hehre, W. J.; Pople, J. A. *J. Chem. Phys.,* 1971, 54, 724-728. (b) Here, W. J.; Ditchfield, R.; Pople, J. A. *J. Chem. Phys.,* 1972, 56, 2257-2261. (c) Hariharan, P. C.; Pople, J. A. *Theor. Chim. Acta,* 1973, 28, 213-222.

13. Chuit, C.; Corriu, R. J. P.; Reye, C.; Young, J. C. *Chem. Rev.,* 1993, 93, 1371-1448.

14. Frisch, M. J. et al. *Gaussian* 03, revision B, 2003, Gaussian, Inc.: Pittsburgh, Pa.

15. (a) Becerra, R.; Walsh, R. *Thermochemistry*, in *The Chemistry of Organic Silicon Compounds*, Rappoport, Z.; Apeloig, Y. Eds. 1998, Vol. 2, page 153. Wiley: Chichester, UK. (b) Walsh, R. *Thermochemistry*, in *The Chemistry of Organic Silicon Compounds*, Patai, S.; Rappoport, Z. Eds. 1989, Vol. 1, page 371. Wiley: Chichester, UK.

We claim:

1. A method of preparing cross-linked silicone polymers comprising contacting a silicone polymer with a hydrolytic enzyme under conditions for the cross-linking of the silicone polymer, wherein the silicone polymer has been modified to comprise $\alpha,\omega$-functional groups that hydrolyze upon contact with the hydrolytic enzyme.

2. The method of claim 1, wherein the silicone polymer and hydrolytic enzyme are further combined with a cross-linking agent.

3. The method according to claim 2, wherein the cross-linking agent is of the formula $SiX_4$, wherein X is any hydrolysable group and each X may be the same or different.

4. The method according to claim 3, wherein each X is the same.

5. The method according to claim 3 wherein X is OR, and wherein R is $C_{1-6}$alkyl.

6. The method according to claim 5, wherein R is methyl or ethyl.

7. The method according to claim 2, comprising:
   (a) mixing the silicone polymer and a cross-linking agent, optionally in a solvent, to provide a first mixture; and
   (b) contacting the first mixture with the hydrolytic enzyme under conditions for the cross-linking of the silicone polymer.

8. The method according to claim 7 wherein step b) is carried out in a solvent selected from water, buffer and organic solvent.

9. The method according to claim 1, wherein the hydrolytic enzyme is a protease.

10. The method according to claim 9, wherein the protease is selected from pepsin $\alpha$-chymostrypsin, bromelain and trypsin.

11. The method according to claim 1 wherein the hydrolytic enzyme is a native enzyme.

12. The method according to claim 11, wherein the hydrolytic enzyme is obtained from a natural product extract.

13. The method according to claim 1, wherein the functional groups are of the formula $L-SiX'_3$, wherein L is a linker group and X' is any hydrolysable group and each X' may be the same or different.

14. The method according to claim 13, wherein each X' is the same.

15. The method according to claim 13 wherein X' is OR', wherein R' is $C_{1-6}$alkyl.

16. The method according to claim 15, wherein R' is methyl or ethyl.

17. The method according to claim 13, wherein L is $C_{1-10}$alkylene.

18. The method according to claim 1, wherein the silicon polymer polydimethylsiloxane.

19. The method according to claim 1 comprising contacting the silicone polymer with the hydrolytic enzyme under conditions for the cross-linking of the silicone polymer optionally in a solvent.

20. The method according to claim 19, wherein the conditions for the cross-linking of the silicone polymer comprise a temperature in the range of about 20° C. to about 40° C.

21. The method according to claim 20, wherein the temperature is about 37° C.

22. The method according to claim 19, wherein contacting comprises mixing for about 1 minute to about 10 minutes.

23. The method according to claim 22, wherein, following contacting with the hydrolytic enzyme, a mixture is formed, which is poured into a mold or is coated onto a substrate.

* * * * *

UNITED STATES PATENT AND TRADEMARK OFFICE
CERTIFICATE OF CORRECTION

PATENT NO. : 8,383,755 B2
APPLICATION NO. : 12/664195
DATED : February 26, 2013
INVENTOR(S) : Paul M. Zelisko, Karen Arnelien and Mark Frampton Page 1 of 1

It is certified that error appears in the above-identified patent and that said Letters Patent is hereby corrected as shown below:

On the title page, item (54) and in the specification, column 1, line 1, in the Title:
"Enzyme-Medicated" Cross-Linking of Silicone Polymers" should read
--Enzyme-Mediated-- Cross-Linking of Silicone Polymers.

In the Claims:

Column 10, line 38, "polymer polydimethylsiloxane" should read --polymer is polydimethylsiloxane--.

Signed and Sealed this
Fourteenth Day of May, 2013

Teresa Stanek Rea
*Acting Director of the United States Patent and Trademark Office*